(12) United States Patent
Schönaich

(10) Patent No.: US 7,874,723 B2
(45) Date of Patent: Jan. 25, 2011

(54) METHOD OF RAPIDLY DETERMINING THE MFR IN THE HIGH-PRESSURE POLYMERIZATION ETHYLENE

(75) Inventor: Dirk Schönaich, Carry le Rouet (FR)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 12/312,497

(22) PCT Filed: Nov. 26, 2007

(86) PCT No.: PCT/EP2007/010241

§ 371 (c)(1),
(2), (4) Date: May 13, 2009

(87) PCT Pub. No.: WO2008/064843

PCT Pub. Date: Jun. 5, 2008

(65) Prior Publication Data

US 2010/0056733 A1 Mar. 4, 2010

Related U.S. Application Data

(60) Provisional application No. 60/876,445, filed on Dec. 21, 2006.

(30) Foreign Application Priority Data

Nov. 27, 2006 (DE) ........................ 10 2006 055 853

(51) Int. Cl.
*C08F 2/00* (2006.01)
*C08F 6/00* (2006.01)
*G01K 17/00* (2006.01)
*G01N 25/18* (2006.01)
*C08F 110/02* (2006.01)

(52) U.S. Cl. ........................... 374/44; 526/352; 526/64; 528/503; 702/136

(58) Field of Classification Search ................. 528/503; 374/44
See application file for complete search history.

(56) References Cited

U.S. PATENT DOCUMENTS 4,087,601 A * 5/1978 Pfleger et al. ............... 526/329

(Continued)

FOREIGN PATENT DOCUMENTS

WO    WO 2004/017056    2/2004

OTHER PUBLICATIONS

Luft, et al. "Effectiveness of Organic Peroxide Initiators in the High-Pressure Polymerization of Ethylene, " *J. Macromol. Sci-Chem*, A11(6), 1089-1112, (1977).

(Continued)

*Primary Examiner*—Fred M Teskin
*Assistant Examiner*—Elizabeth Eng
(74) *Attorney, Agent, or Firm*—Jonathan L. Schuchardt

(57) ABSTRACT

Method of determining the melt mass flow rate of an ethylene polymer in the polymerization of ethylene or of ethylene with further comonomers, which is carried out at temperatures of from 140° C. to 350° C. and pressures of from 40 MPa to 350 MPa in a reactor to form the ethylene polymer and the ethylene polymer is subsequently cooled in a heat exchanger, which comprises: a) establishment of a correlation between the thermal conductivity of the ethylene polymer in the heat exchanger and the melt mass flow rate of the ethylene polymer, with the individual measurements each being carried out at an essentially constant melt mass flow rate, b) measurement of the thermal conductivity of an ethylene polymer in the heat exchanger c) calculation of the melt mass flow rate from the thermal conductivity measured in b) and the correlation established in a).

6 Claims, 1 Drawing Sheet

U.S. PATENT DOCUMENTS

Figure 1:
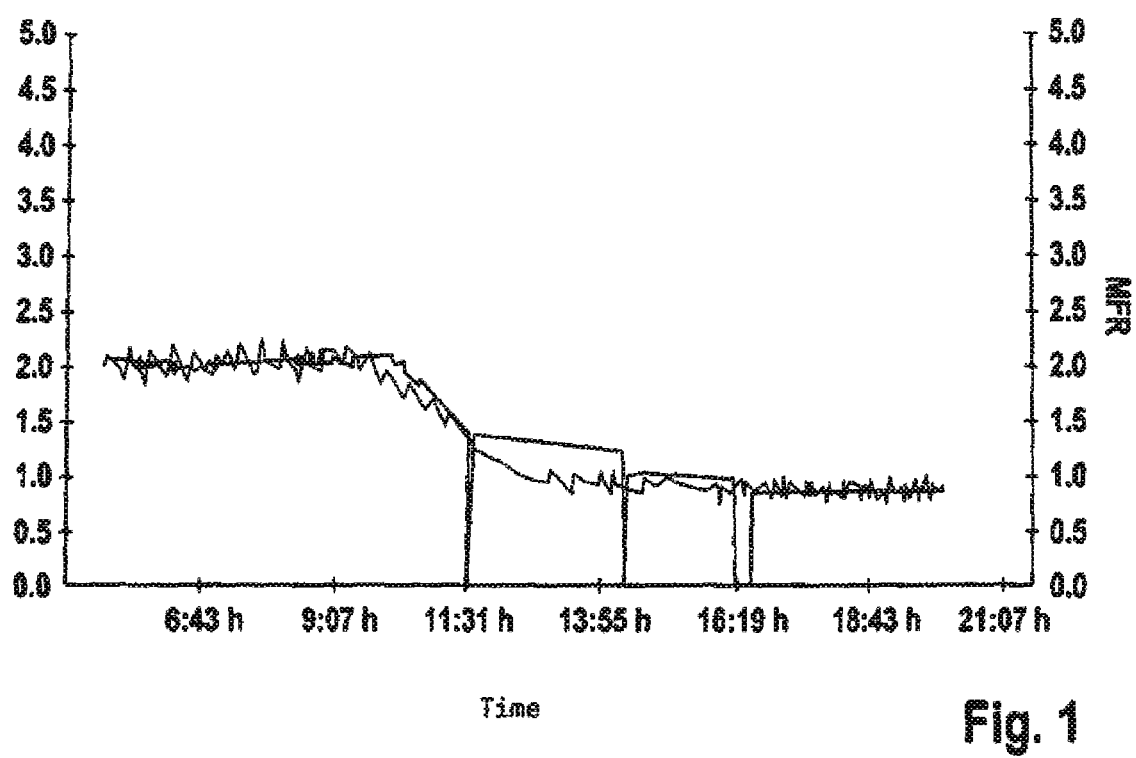

| | | | |
|---|---|---|---|
| 4,933,886 A * | 6/1990 | George | 702/47 |
| 6,543,934 B1 | 4/2003 | Hammer et al. | |
| 6,547,995 B1 * | 4/2003 | Comb | 264/40.1 |
| 6,677,408 B1 | 1/2004 | Mahling et al. | |
| 2006/0167193 A1 | 7/2006 | Mahling et al. | |

OTHER PUBLICATIONS

Mahling, et al. "Modellierung der Ethylen-Polymerisation im Elenac-Hochdruk-Rohrreaktorverfahren," Chem. Ing. Tech., 71, 1301, (1999).

Busch, M., "Modeling Kinetics and Structural Properties in High-Pressure Fluid-Phase Polymerization," Macromol. Theory Simul. 10, Properties in 408-429, (2001).

* cited by examiner

METHOD OF RAPIDLY DETERMINING THE MFR IN THE HIGH-PRESSURE POLYMERIZATION ETHYLENE

CROSS-REFERENCE TO RELATED APPLICATIONS

This application is a national phase filing under 35 U.S.C. §371 of International Application PCT/EP2007/010241, filed Nov. 26, 2007, claiming priority to German Patent Application 102006055853.7 filed Nov. 27, 2006 and provisional U.S. Appl. No. 60/876,445 filed Dec. 21, 2006; the disclosures of International Application PCT/EP2007/010241, German Pat. Appl. 102006055853.7, and U.S. Appl. No. 60/876,445, each as filed, are incorporated herein by reference.

The invention relates to a method of rapidly determining the melt mass flow rate in the high-pressure polymerization of ethylene.

The high-pressure polymerization process continues to be a valued process for preparing low density polyethylene (LDPE) which is carried out very successfully worldwide on an industrial scale in numerous plants. In the high-pressure polymerization, the polymerization is usually initiated by means of atmospheric oxygen or by means of peroxides or by means of other free-radical formers or by means of mixtures of these.

In the high-pressure polymerization, the reaction gas is firstly heated to a temperature in the range from 90 to 200° C. in order to start the strongly exothermic polymerization reaction. The heat of reaction which is then liberated in the actual polymerization is removed by water cooling; generally up to 30% of the monomers used are converted into polymer in one pass through the continuously operated tube reactor.

A very important parameter for characterizing LDPE is its melt mass flow rate (MFR) in accordance with ISO 1133, since it is, apart from the density of the polyethylene and the amount and type of additives added, the feature which is generally used for the specification of various LDPE sales products. Apart from the density and the additive content, it is the parameter which serves to define the various product types. The melt mass flow rate (MFR) is the most important directly influenceable quality parameter of low density polyethylene (LDPE).

In existing plants, this parameter is determined in various ways:
1. Manual, discontinuous sampling of pellets between extruder and devolatilization hoppers and subsequent manual measurement.
2. Automatic, continuous sampling between extruder and devolatilization hoppers and also automatic, continuous measurement by means of calibrated viscosity measurement apparatuses.

Both methods have the disadvantage that the MFR of the product actually produced can be determined only after a dead time of 20-45 minutes (residence time of the product between reactor outlet and sampling point plus measurement time).

During start-up of the plant and in the case of changes of product type, the MFR is the parameter which, owing to the above-described method, takes up the most time and thus determines the amount of out-of-specification product produced. There is therefore a great need to determine the MFR of the product as close as possible to production.

It was an object of the present invention to provide a process for the high-pressure polymerization of ethylene by means of which quantities of out-of-specification polymer can be largely avoided. This also applies particularly to start-up and product change procedures.

The present invention was based on the recognition that the heat transfer coefficient in the heat exchanger at the reactor outlet (after-cooler) of a high-pressure reactor depends on the viscosity and thus also the melt mass flow rate of the product and can be correlated with this.

Accordingly, a method of determining the melt mass flow rate of an ethylene polymer in the polymerization of ethylene or of ethylene with further comonomers, which is carried out at temperatures of from 140° C. to 350° C. and pressures of from 40 MPa to 350 MPa in a reactor to form the ethylene polymer and the ethylene polymer is subsequently cooled in a heat exchanger, which comprises the steps:
a) establishment of a correlation between the thermal conductivity of the ethylene polymer in the heat exchanger and the melt mass flow rate of the ethylene polymer, with the individual measurements each being carried out at an essentially constant melt mass flow rate,
b) measurement of the thermal conductivity of an ethylene polymer in the heat exchanger,
c) calculation of the melt mass flow rate from the thermal conductivity measured in b) and the correlation established in a),
is provided.

The method makes it possible to determine the melt mass flow rate (MFR) of the polymer as soon as it leaves the reactor and flows through the after-cooler. It is not necessary to wait for the residence time of the product after leaving the after-cooler until the result of the analysis is obtained.

In this way, the MFR can be determined significantly earlier and the quantity of out-of-specification product produced during start-up and changes of product type can thus be significantly reduced. Furthermore, it makes it possible to recognize deviations of the MFR in steady-state operation of the plant significantly earlier than has hitherto been the case. It is possible to undertake corrective interventions before a deviation can be determined by conventional methods. This can likewise mean that the production of out-of-specification product is avoided. In any case, it makes it possible to keep the MFR within a narrow range.

In step a), a correlation between the thermal conductivity and the melt mass flow rate is firstly determined. This is preferably achieved by determining the heat transfer coefficient which represents a measure of the thermal conductivity after equilibrium has been attained in the cooler. In the simplest case, it is sufficient to determine a correlation for the respective product types, i.e. for each MFR (at one and the same density) and for each density. Although the density itself has no significant influence on the heat transfer coefficient, the correlation shifts as a result of higher densities being produced under other process conditions (pressure, temperature). The empirical formula resulting therefrom then makes it possible to determine the MFR quantitatively by means of the heat transfer coefficient of the after-cooler. In the simplest case (coverage of a relatively small bandwidth of various MFRs), a linear relationship between heat transfer coefficient and MFR can be used. In addition, all customary data correlation methods can in principle be used.

The melt mass flow rate (MFR) is determined here by conventional analysis, for example in accordance with ISO 1133, of the polymer product. The most frequently used conditions are 190° C. and a weight of 2.16, 5 or 21.6 kg.

The heat transfer coefficient can be calculated, for example, from the thermal balance in accordance with the formula (I)

$$dm/dt \, c_p (T_R^{in} - T_R^{out}) = k \, A \, \Delta T_m \tag{I}$$

without being restricted thereto, where the parameters have the following meanings:
dm/dt: mass flow of the reaction mixture
$c_p$: heat capacity of the reaction mixture k: heat transfer coefficient
A: heat transfer surface area of after-cooler
$T_R^{in}$, $T_R^{out}$: temperature of the reaction mixture on entry into or exit from the cooler
$\Delta T_m$: mean temperature difference between the cooling medium (pressurized water) and the reaction mixture.

To obtain information about the trend in the MFR, it is sufficient to monitor the heat transfer coefficient by means of measured values determined with the aid of existing measuring instruments, e.g. temperature of the reaction mixture at the inlet and outlet of the after-cooler ($T_R^{in}$, $T_R^{out}$) and the temperature of the cooling water at the inlet and outlet of the after-cooler, without carrying out an absolute calculation. A decreasing heat transfer coefficient indicates a decreasing MFR and vice versa.

Depending on the plant configuration, some variables can remain constant in the calculation of the heat transfer coefficient, so that the correlation of the MFR can be carried out directly with the temperatures of the reaction mixture at the inlet and outlet of the after-cooler. This simplifies the determination of the heat transfer coefficient without influencing the result.

However, the after-cooler can display different behavior in the long term, for example as a result of polymer deposits, which is why it is advantageous also to check the correlation with the MFR continually. This can be achieved, for example, by a regular set-actual comparison of the MFR sensor with the MFR measured in-line on the product with a time delay.

The method of the invention can be employed only when the after-cooler has reached an at least approximately constant operating temperature. This restriction means that the MFR which is determined by the method of the invention during the first minutes after start-up of the polymerization does not coincide with the actual value. The reason for this is that the metal of the after-cooler still takes up heat up to this point in time and therefore gives a false value deviating from the actual heat transfer coefficient. Only after thermal equilibrium has been established in the after-cooler are reliable data produced. However, compared to the time taken to set the MFR after start-up, this phase is so short that its significance is negligible.

The method of the invention is particularly advantageous when the polymerization initiator mixtures are metered in continuously and essentially pulsation-free, since a uniform initiator concentration profile is established under such conditions and no fluctuations interfere in the optimization process.

The method of the invention can be used both for the homopolymerization of ethylene and for the copolymerization of ethylene with one or more other monomers, provided that these monomers are free-radically copolymerizable with ethylene under high pressure. Examples of suitable copolymerizable monomers are α,β-unsaturated $C_3$-$C_8$-carboxylic acids, in particular maleic acid, fumaric acid, itaconic acid, acrylic acid, methacrylic acid and crotonic acid, derivatives of α,β-unsaturated $C_3$-$C_8$-carboxylic acids, e.g. unsaturated $C_3$-$C_{15}$-carboxylic esters, in particular esters of $C_1$-$C_6$-alkanols, or anhydrides, in particular methyl methacrylate, ethyl methacrylate, n-butyl methacrylate or tert-butyl methacrylate, methyl acrylate, ethyl acrylate, n-butyl acrylate, 2-ethylhexyl acrylate, tert-butyl acrylate, methacrylic anhydride, maleic anhydride or itaconic anhydride, and α-olefins such as propene, 1-butene, 1-pentene, 1-hexene, 1-octene or 1-decene. In addition, vinyl carboxylates, particularly preferably vinyl acetate, can be used as comonomers. n-Butyl acrylate, acrylic acid or methacrylic acid are particularly advantageously used as comonomer. The proportion of comonomer or comonomers in the reaction mixture is from 1 to 45% by weight, preferably from 3 to 30% by weight, based on the amount of ethylene. In the case of copolymerization, the further monomers are preferably fed in at a plurality of different points on the reactor.

For the purposes of the present invention, polymers are all substances which are made up of at least two monomer units. They are preferably LDPE polymers having a mean molecular weight $M_n$ of more than 20 000 g. However, the method of the invention can also be advantageously employed in the preparation of oligomers, waxes and polymers having a molecular weight $M_n$ of less than 20 000 g.

Possible initiators for starting the polymerization in the respective reaction zone are, for example, air, oxygen, azo compounds or peroxidic polymerization initiators. Initiation using organic peroxides or azo compounds represents a particularly preferred embodiment of the method of the invention. Examples of suitable organic peroxides are peroxy esters, peroxy ketals, peroxy ketones and peroxycarbonates, e.g. di(2-ethylhexyl)peroxydicarbonate, dicyclohexyl peroxydicarbonate, diacetyl peroxydicarbonate, tert-butyl peroxyisopropylcarbonate, di-tert-butyl peroxide, di-tert-amyl peroxide, dicumyl peroxide, 2,5-dimethyl-2,5-di-tert-butylperoxyhexane, tert-butyl cumyl peroxide, 2,5-dimethyl-2,5-di(tert-butylperoxy)hex-3-yne, 1,3-diisopropyl monohydroperoxide or tert-butyl hydroperoxide, didecanoyl peroxide, 2,5-dimethyl-2,5-di(2-ethyl-hexanoylperoxy)hexane, tert-amyl peroxy-2-ethylhexanoate, dibenzoyl peroxide, tert-butyl peroxy-2-ethylhexanoate, tert-butyl peroxydiethylacetate, tert-butyl peroxydiethylisobutyrate, 1,1-di(tert-butylperoxy)-3,3,5-trimethylcyclohexane, 1,1-di(tert-butylperoxy)cyclohexane, tert-butyl peroxyacetate, cumyl peroxyneodecanoate, tert-amyl peroxyneodecanoate, tert-amyl peroxypivalate, tert-butyl peroxyneodecanoate, tert-butyl permaleate, tert-butyl peroxypivalate, tert-butyl peroxyisononanoate, diisopropylbenzene hydroperoxide, cumene hydroperoxide, tert-butyl peroxybenzoate, methyl isobutyl ketone hydroperoxide, 3,6,9-triethyl-3,6,9-trimethyl-triperoxocyclononane and 2,2-di(tert-butylperoxy)butane. Azoalkanes (diazenes), azodicarboxylic esters, azodicarboxylic dinitriles such as azobisisobutyronitrile and hydrocarbons which decompose into free radicals and are also referred as C-C initiators, e.g. 1,2-diphenyl-1,2-dimethylethane derivatives and 1,1,2,2-tetramethylethane derivatives, are also suitable. It is possible to use either individual initiators or preferably mixtures of various initiators. A large range of initiators, in particular peroxides, are commercially available, for example the products of Akzo Nobel offered under the trade names Trigonox® or Perkadox®.

In a preferred embodiment of the process of the invention, peroxidic polymerization initiators having a relatively high decomposition temperature are used. Suitable peroxidic polymerization initiators include, for example, 1,1-di(tert-butylperoxy)cyclohexane, 2,2-di(tert-butylperoxy)butane, tert-butyl peroxy-3,5,5-trimethylhexanoate, tert-butyl peroxybenzoate, 2,5-dimethyl-2,5-di-tert-butylperoxyhexane, tert-butyl cumyl peroxide, di-tert-butyl peroxide and 2,5-dimethyl-2,5-di(tert-butylperoxy)hex-3-yne, and particular preference is given to using di-tert-butyl peroxide.

In an advantageous embodiment of the present invention, the polymerization takes place in a tube reactor.

The polymerization is preferably carried out in a tube reactor having a plurality of reaction zones, more preferably 2-6 reaction zones, particularly preferably from 3 to 5 reaction zones. In each polymerization zone, the polymerization is initiated by addition of the initiators which decompose into free radicals. The tube reactor preferably has a length-to-diameter ratio of >1000.

In the preparation of highly viscous products, e.g. MFR=0.25 g/10 min, it is advantageous to add the monomer or monomers not only at the inlet of the reactor tube but to feed in monomers at a plurality of different points on the reactor. This is particularly preferably done at the beginning of the further reaction zones.

The initiators can be employed individually or as a mixture in concentrations of from 0.1 to 50 mol/t of polyethylene produced, in particular from 0.2 to 20 mol/t, in each zone. It is often advantageous to use the initiators in the dissolved state. Examples of suitable solvents are ketones and aliphatic hydrocarbons, in particular octane, decane and isododecane and also other saturated $C_8$-$C_{25}$-hydrocarbons. The solutions comprise the initiator mixtures in proportions of from 2 to 65% by weight, preferably from 5 to 40% by weight and particularly preferably from 10 to 30% by weight. Particular preference is given to using mixtures of initiators which have different decomposition temperatures.

In the process of the invention, the molar mass of the polymers to be prepared can as usual be controlled by addition of molecular weight regulators. Examples of suitable regulators are hydrogen, aliphatic and olefinic hydrocarbons, e.g. pentane, hexane, cyclohexane, propene, 1-pentene or 1-hexene, ketones such as acetone, methyl ethyl ketone (2-butanone), methyl isobutyl ketone, methyl isoamyl ketone, diethyl ketone or diamyl ketone, aldehydes such as formaldehyde, acetaldehyde or propionaldehyde and saturated aliphatic alcohols such as methanol, ethanol, propanol, isopropanol or butanol. Particular preference is given to using saturated aliphatic aldehydes, in particular propionaldehyde or α-olefins such as propene or 1-hexene. The molecular weight regulators are preferably added to the reaction mixture upstream of the tube reactor. It can also be introduced together with the polymerization initiator at one or more points along the tube reactor. The addition of the regulator can be incorporated into the optimization process.

The process of the invention is usually carried out at pressures of from 1000 to 4000 bar, with pressures of from 1800 to 3500 bar being preferred and pressures of from 2000 to 3300 bar being particularly preferred. The temperatures are generally in the range from 100 to 350° C., preferably from 140 to 340° C. and very particularly preferably from 150° C. to 320° C. In the case of copolymerization of ethylene with sensitive or strongly regulating comonomers, in particular free-radically polymerizable carboxylic esters, e.g. vinyl esters, the polymerization is preferably carried out at temperatures below 230° C. In general, preference is given to a process in which the polymerization temperature is no higher than 320° C.

The flowing reaction mixture generally comprises polyethylene in an amount in the range from 0 to 45% by weight, based on the total weight of the monomers fed to the reactor, usually up to 40% by weight.

Since MFR data which are very close to the process can be provided by means of the MFR monitor of the invention, it is particularly advantageous to couple the data obtained by means of the MFR monitor with a kinetic reaction model which likewise allows prediction of product data such as the MFR. As a result of the rapid back-coupling with data which are close to the process, the prediction can be continually modified and the accuracy can thereby be improved considerably.

The basic principles of such a system are explained below.

The implementation requires a model for the reaction system in order to be able to calculate the influence of the various polymerization initiators on the reaction temperature and thus also on the product properties. A system of differential equations which should replicate the reaction kinetics in the reactor and the mass and heat balances as accurately as possible is usually used for this purpose. Such models are prior art and form the basis of all advanced process controllers which operate on a "first principles" basis, as have been used for some time for the control and regulation of chemical reaction processes. Such reaction models are described, for example, in "Modellierung der Ethylen-Polymerisation im Elenac-Hochdruck-Rohrreaktorverfahren", F. -O. Mähling, R. Klimesch, M. Schwibach, M. Buback, M. Busch, Chem. Ing. Tech. 71, 1301 (1999), G. Luft, H. Bitsch, H. Seidl, J. Macromol. Sci.-Chem., All (6), 1089 (1977) and in M. Busch, Macromol. Theory Simul. 10, 408 (2001).

To calculate the optimal composition of the initiator mixture and the optimal reaction conditions, the use of a computer-aided tool for rapidly solving the system of differential equations is indispensable. Many such tools are commercially available. Further details regarding the computer program "Muscod II" used here may be found in Forschrittsbericht des VDI, Series 3: Verfahrenstechnik, No. 613, 1999, in which the principles of the program and examples of its use are described in more detail.

A further prerequisite for the implementation of efficient regulation is sufficiently rapid determination of the physical parameters in the reactor. Temperature measurement is preferably carried out using a temperature sensor having short response times, as is described in WO 97/25601.

Furthermore, the mass flow of the various initiators into the reactor should preferably be continuous and as pulsation-free as possible in order to achieve good regulation. For this purpose, it is possible to use, for example, the metering device described in WO 00/77055, by means of which rapid, uniform mixing of polymerization initiator fed in and reaction mixture is ensured.

While the molar mass $M_w$ can be influenced very well by means of the added regulators independently of the initiators, determination of the product properties, in particular the density and the melt mass flow rate (MFR), close to production is of great advantage for precise regulation. The method of the invention of determining the MFR is particularly useful for precisely this purpose. To determine the density, samples are taken and the density is calculated from an IR or Raman spectrum. On-line determination of the density is also possible. The methods mentioned are generally known to those skilled in the art or are described in DE 102 37 394. These possible ways of determining product properties close to the process can also be incorporated into the regulation process, as a result of which the proportion of reject product which does not meet the required specification can be reduced further.

In a further advantageous embodiment of the present invention, the tube reactor is preceded by an autoclave by means of which a prepolymerization at a lower temperature above about 80° C. is possible.

A detailed description of a suitable regulation system may be found in WO 2004/078800.

All documents cited are expressly incorporated by reference into the present patent application. All percentages in this patent application are by weight based on the total weight of the respective mixtures, unless indicated otherwise.

The invention is illustrated below with the aid of examples, without being restricted thereto.

EXAMPLES

The polymerization was carried out in a high-pressure tube reactor having a length of 2200 m and a diameter of 76 mm. The reactor had 4 reaction zones and initiator was metered into the reactor at the beginning of each of these. The pressure at the reactor inlet was 2800 bar and the ethylene throughput was 116 t/h. The after-cooler had a length of 480 m and an internal diameter of 76 mm. A process control system from Hartmann and Braun was used. Propionaldehyde served as regulator.

The heat transfer coefficient was determined from the reaction parameters with the aid of the formula (I).

FIG. 1 depicts the course of the MFR determined by means of the method of the invention and the MFR determined by conventional means at a change of product type. The determination by conventional means was carried out on the finished pellets in accordance with ISO 1133. The sawtooth curve results from the bleeding, viz. a regular opening of the pressure maintenance valve, which causes a sudden pressure drop and briefly allows the temperature to rise sharply. The use of suitable filters enables the curve to be smoothed. When the process is carried out without bleeding, this slight interference in the determination of the MFR does not occur. In any case, the interference is inconsequential since it occurs for a few seconds once per minute; the changes in the MFR to be observed occur over significantly longer periods of time. The sharp drops in the comparative curve determined by conventional means are attributable to brief interruptions in operation of the measuring instrument.

It can clearly be seen that the MFR values determined by the method of the invention response significantly earlier to the changes in the composition in the reactor. The dead time can be significantly reduced by means of the method of the invention. Compared to the MFR determined by the method of the invention, the conventional determination of the MFR has a time delay of about 30 minutes.

In the example described, the method used reduces the production of out-of-specification material in three places:

1. To prevent out-of-specification product contaminating a batch, the product immediately after implementation of a product change is usually discarded. The novel method enables the product to be allocated to the in-specification batch until the MFR is actually outside the specification.
2. The method presented makes it possible to recognize whether the MFR approximates the desired value earlier than hitherto. Here too, earlier corrective interventions reduce the amount of out-of-specification product produced.
3. The method presented makes it possible to activate transfer to the new hopper for in-specification product earlier than hitherto, since the correct MFR is recognized earlier. It is merely necessary to wait for the (short and known) residence time of the product between after-cooler and pellet dryer. In this way, it is ensured that out-of-specification product which is still present in the lines and apparatuses downstream of the after-cooler does not contaminate the new batch of in-specification product.

The invention claimed is:

1. A method of determining the melt mass flow rate of an ethylene polymer in the polymerization of ethylene or of ethylene with further comonomers, wherein the polymerization is carried out at temperatures of from 140° C. to 350° C. and pressures of from 40 MPa to 350 MPa in a reactor to form the ethylene polymer, and wherein the ethylene polymer is subsequently cooled in a heat exchanger, said method comprising:
   a) establishing a correlation between the thermal conductivity of the ethylene polymer in the heat exchanger and the melt mass flow rate of the ethylene polymer, with individual measurements each being carried out at an essentially constant melt mass flow rate,
   b) measuring the thermal conductivity of the ethylene polymer in the heat exchanger; and
   c) calculating the melt mass flow rate from the thermal conductivity measured in b) and the correlation established in a).

2. The method of claim 1 wherein steps b) and c) are carried out continuously.

3. The method of claim 1 wherein step a) is carried out discontinuously at regular intervals.

4. The method of claim 1 wherein step a) is carried out immediately before a change to a product having an altered melt mass flow rate.

5. A process which comprises polymerizing ethylene or ethylene with further comonomers wherein the process comprises the determination method of claim 1.

6. The process of claim 5 wherein the polymerization is performed in a tube reactor having a length-to-diameter ratio of more than 1000.

* * * * *